US010925963B2

(12) United States Patent
Goldberg et al.

(10) Patent No.: US 10,925,963 B2
(45) Date of Patent: Feb. 23, 2021

(54) COMBINATION ARTEMISININ AND CHEMILUMINESCENT PHOTODYNAMIC THERAPY AND USES THEREFOR

(71) Applicant: Washington University, St. Louis, MO (US)

(72) Inventors: Daniel E. Goldberg, St. Louis, MO (US); Paul Sigala, St. Louis, MO (US)

( * ) Notice: Subject to any disclaimer, the term of this patent is extended or adjusted under 35 U.S.C. 154(b) by 289 days.

(21) Appl. No.: 15/189,655

(22) Filed: Jun. 22, 2016

(65) Prior Publication Data
US 2016/0367674 A1 Dec. 22, 2016

Related U.S. Application Data

(60) Provisional application No. 62/183,042, filed on Jun. 22, 2015.

(51) Int. Cl.
*A61K 41/00* (2020.01)
*A61K 31/502* (2006.01)
*A61K 31/366* (2006.01)
*A61K 31/197* (2006.01)

(52) U.S. Cl.
CPC ........ *A61K 41/0061* (2013.01); *A61K 31/197* (2013.01); *A61K 31/366* (2013.01); *A61K 31/502* (2013.01); *Y02A 50/30* (2018.01)

(58) Field of Classification Search
CPC . A61K 41/0061; A61K 31/197; A61K 31/366
See application file for complete search history.

(56) References Cited

U.S. PATENT DOCUMENTS

| 8,603,985 | B2 | 12/2013 | Weissbach et al. |
| 2013/0108710 | A1* | 5/2013 | Tanaka .................. A61K 31/197 424/648 |

OTHER PUBLICATIONS

Ariey, F. et al., "A molecular marker of artemisinin-resistant Plasmodium falciparum malaria," HHS Public Access Author Manuscript, available in PMC Sep. 1, 2016, pp. 1-28, Published in final edited form as: Nature, Jan. 2, 2014, pp. 50-55, vol. 505, No. 7481.
Balu, B., et al., "High-efficiency transformation of Plasmodium falciparum by the lepidopteran transposable element piggyback," PNAS, Nov. 8, 2005, pp. 16391-16396, vol. 102, No. 45.
Baptista, M. et al., "Photodynamic antimicrobial chemotherapy (PACT) for the treatment of malaria, leishmaniasis and trypanosomiasis," Braz. J. Med. Biol. Res., Jan. 2011, pp. 1-10, vol. 44, No. 1.
Beck, J. et al., "HSP101/PTEX mediates export of diverse malaria effector proteins into the host erythrocyte," HHS Public Access Author Manuscript, available in PMC Jan. 31, 2015, pp. 1-24, Published in final edited form as: Nature, Jul. 31, 2014, pp. 592-595, vol. 511, No. 7511.
Bissonnette, R., et al., "Oral Aminolevulinic Acid Induces Protoporphyrin IX Fluorescence in Psoriatic Plaques and Peripheral Blood Cells," Photochem. Photobiol., 2001, pp. 339-345, vol. 74, No. 2.
Celli, J. et al., "Imaging and Photodynamic Therapy: Mechanisms, Monitoring and Optimization," NIH Public Access Author Manuscript, available in PMC May 12, 2011, pp. 1-96, Published in final edited form as: Chem. Rev., May 12, 2010, pp. 2795-2838, vol. 110, No. 5.
Chen, T-C. et al., "Luminol as the light source for in situ photodynamic therapy," Process Biochem., 2012, pp. 1903-1908, vol. 47, No. 12, Elsevier Ltd.
Cobbold, S. et al., "Methionine transport in the malaria parasite *Plasmodium falciparum*," Int. J. Parasitol., Jan. 2011, pp. 125-135, vol. 41, No. 1.
Dahl, E. et al., "Tetracyclines Specifically Target the Apicoplast of the Malaria Parasite *Plasmodium falciparum*," Antimicrob. Agents Chemother., Sep. 2006, pp. 3124-3131, vol. 50, No. 9.
Desai, S. et al., "A voltage-dependent channel involved in nutrient uptake by red blood cells infected with the malaria parasite," Nature, Aug. 31, 2000, pp. 1001-1005, vol. 406, No. 6799.
Fotinos, N. et al., "5-Aminolevulinic Acid Derivatives in Photomedicine: Characteristics, Application and Perspectives," Photochem. Photobiol., 2006, pp. 994-1015, vol. 82, No. 4.
Genbank Accession No. CBL55989.1, Feb. 27, 2015, 2 pgs.
Ginsburg, H. et al., "Characterization of Permeation Pathways Appearing in the Host Membrane of Plasmodium Falciparum Infected Blood Cells," Mol. Biochem. Parasitol., Mar. 1985, pp. 313-322, vol. 14, No. 3.
Gordi, T. et al., "Artemisinin derivatives: toxic for laboratory animals, safe for humans?," Toxicol. Lett., Mar. 1, 2004, pp. 99-107, vol. 147, No. 2.
Izumo, A. et al., "A method for monitoring the viability of malaria parasites (*Plasmodium yoelii*) freed from the host erythrocytes," Trans. R. Soc. Trop. Med. Hyg., 1987, pp. 264-267, vol. 81.
Kamidate, T. et al., "Application of 4-Iodophenol-enhanced Luminol Chemiluminescence to Direct Detection of Horseradish Peroxidase Encapsulated in Liposomes," Japan Soc. Anal. Sci., Sep. 2009, pp. 1163-1166, vol. 25.
Ke, H. et al., "The Heme Biosynthesis Pathway is Essential for Plasmodium falciparum Development in Mosquito Stage but Not in Blood Stages," J. Biol. Chem., Dec. 12, 2014, pp. 34827-34837, vol. 289, No. 50.
Kennedy, J. et al., "Photodynamic Therapy With Endogenous Protoporphyrin IX: Basic Principles and Present Clinical Experience," J. Photochem. Photobiol., B: Biol., 1990, pp. 143-148, vol. 3.
Kirk, K. et al., "Transport of Diverse Substrates into Malaria-infected Erythrocytes via a Pathway Showing Functional Characteristics of Chloride Channel," J. Biol. Chem., Feb. 4, 1994, pp. 3339-3347, vol. 269, No. 5.

(Continued)

*Primary Examiner* — Pancham Bakshi
(74) *Attorney, Agent, or Firm* — Polsinelli PC

(57) ABSTRACT

Photodynamic therapy-based methods of treating diseases such as cancer and malaria are disclosed. These methods include administering 5-aminolevulinic acid (ALA), luminol and artemisinin (ART). ART and ALA administered in combination with luminol can kill malaria parasites without host toxicity. In some aspects, the methods further include administration of a luminol enhancer such as 4-iodophenol. The disclosed methods can also be used to remove potential malaria pathogens from the blood supply.

20 Claims, 13 Drawing Sheets
(13 of 13 Drawing Sheet(s) Filed in Color)

Specification includes a Sequence Listing.

(56) References Cited

OTHER PUBLICATIONS

Klemba, M. et al., "Trafficking of plasmepsin II to the food vacuole of the malaria parasite *Plasmodium falciparum*," J. Cell Biol., 2003, pp. 47-56, vol. 164, No. 1.

Laptev, R. et al., "Intracellular chemiluminescence activates targeted photodynamic destruction of leukaemic cells," Br. J. Cancer, 2006, pp. 189-196, vol. 95.

Larkin, T. et al., "Illuminating the health and safety of luminol," Sci. Justice, Jun. 2008, pp. 71-75, vol. 48, No. 2.

Li, Y. et al., "Dihydroartemisinin Accentuates the Anti-Tumor Effects of Photodynamic Therapy via Inactivation of NF-κB Eca109 and Ec9706 Esophageal Cancer Cells," Cell Physiol. Biochem., 2014, pp. 1527-1536, vol. 33.

Mamoun, C. et al., "A set of independent selectable markers for transfection of the human malaria parasite *Plasmodium falciparum*," PNAS, Jul. 1999, pp. 8716-8720, vol. 96, with Correction, pp. 10943-10944.

Nagaraj, V. et al., "Malaria Parasite-Synthesized Heme Is Essential in the Mosquito and Liver Stages and Complements Host Heme in the Blood Stages of Infection," PLoS Pathogens, Aug. 2013, pp. 1-13, vol. 9, No. 8, e1003522.

Ponka, P., "Cell Biology of Heme," Am. J. Med. Sci., Oct. 1999, pp. 241-256, vol. 318, No. 4.

Ponpuak, M. et al., "A role for falcilysin in transit peptide degradation in the Plasmodium falciparum apicoplast," Mol. Microbiol., 2007, pp. 314-334, vol. 63, No. 2.

Rose, A. et al., "Chemiluminescence of Luminol in the Presence of Iton(II) and Oxygen: Oxidation Mechanism and Implications for Its Analytical Use," Anal. Chem., Dec. 2001, pp. 5909-5920, vol. 73, No. 24.

Sattler, I. et al., "Cloning, Sequencing, and Expression of the Uroporphyrinogen III Methyltransferase cobA Gene of Propionibacterium freudenreichii (shermanii)," J. Bacteriol., Mar. 1995, pp. 1564-1569, vol. 177, No. 6.

Sidhu, A. et al., "Chloroquine Resistance in Plasmodium falciparum Malaria Parasites Conferred by pfcrt Mutations," Sci., Oct. 4, 2002, pp. 210-213, vol. 298, No. 5591.

Sigala, P. et al., "Direct Tests of Enzymatic Heme Degradation by the Malaria Parasite *Plasmodium falciparum*," J. Biol. Chem., Nov. 2, 2012, pp. 37793-37807, vol. 287, No. 45.

Sigala, P. et al., "The Peculiarities and Paradoxes of Plasmodium Heme Metabolism," Ann. Rev. Microbiol., May 31, 2014, pp. 259-278, vol. 68.

Smith, T. et al., "Inactivation of Plasmodium falciparum by Photodynamic Excitation of Heme-Cycle Intermediates Derived from delta-Aminolevulinic Acid," J. Infectious Diseases, Jul. 1, 2004, pp. 184-191, vol. 190.

Spillman, N. et al., "Protein Export into Malaria Parasite-Infected Erythrocytes: Mechanisms and Functional Consequences," Annu. Rev. Biochem., 2015, pp. 813-841, vol. 84.

Staines, H. et al., "Furosemide analogues as potent inhibitors of the new permeability pathways of Plasmodium falciparum-infected human erythrocytes," Mol. Biochem. Parasitol., Feb. 2004, pp. 315-318, vol. 133, No. 2.

Surolia, N. et al., "De Novo Biosynthesis of Heme Offers a New Chemotherapeutic Target in the Human Malarial Parasite," Biochem. Biophys. Res. Commun., Sep. 16, 1992, pp. 744-750, vol. 187, No. 2.

Thorpe, G. et al., "Enhanced Chemiluminescent Reactions Catalyzed by Horseradish Peroxidase," Methods Enzymol., 1986, pp. 331-353, vol. 133.

Tonkin, C. et al., "Localization of organellar proteins in Plasmodium falciparum using a novel set of transfection vectors and a new immunofluorescence fixation method," Mol. Biochem. Parasitol., 2004, pp. 13-21, vol. 137.

Wildt, S. et al., "cobA, a red fluorescent transcriptional reporter for *Escherichia coli*, yeast, and mammalian cells," Nat. Biotechnol., Dec. 1999, pp. 1175-1178, vol. 17, No. 12.

Yeh, E. et al., "Chemical Rescue of Malaria Parasites Lacking an Apicoplast Defines Organelle Function in Blood-Stage Plasmodium falciparum," PLoS Biol., Aug. 2011, vol. 9, No. 8, e1001138.

Yuan, H. et al., "Chemical Molecule-Induced Light-Activated System for Anticancer and Antifungal Activities," J. Am. Chem. Soc., 2012, pp. 13184-13187, vol. 134, No. 32.

Zhang, S. et al., "Heme Mediates Cytotoxicity from Artemisinin and Serves as a General Anti-Proliferation Target," PLoS One, Oct. 2009, pp. 1-10, vol. 4, No. 10, e7472.

\* cited by examiner

Prior Art parasite-infected erythrocytes
normal permeability: ALA + TMP blocked permeability: ALA - TMP normal uptake
ALA +furosemide
blocked uptake
ALA

SEQUENCE LISTING

```
<160> NUMBER OF SEQ ID NOS: 8

<210> SEQ ID NO 1
<211> LENGTH: 46
<212> TYPE: DNA
<213> ORGANISM: Artificial Sequence
<220> FEATURE:
<223> OTHER INFORMATION: SYNTHESIZED

<400> SEQUENCE: 1 acgattttt ctcgagatga ccaccacact gttgcccggc actgtc         46

<210> SEQ ID NO 2
<211> LENGTH: 38
<212> TYPE: DNA
<213> ORGANISM: Artificial Sequence
<220> FEATURE:
<223> OTHER INFORMATION: SYNTHESIZED

<400> SEQUENCE: 2
ctgcacctgg cctagggtgg tcgctgggcg cgcgatgg                 38

<210> SEQ ID NO 3
<211> LENGTH: 58
<212> TYPE: DNA
<213> ORGANISM: Artificial Sequence
<220> FEATURE:
<223> OTHER INFORMATION: SYNTHESIZED

<400> SEQUENCE: 3
cactatagaa ctcgaggatc ataataatga tacattatgt actattggga catcgtcc    58

<210> SEQ ID NO 4
<211> LENGTH: 56
<212> TYPE: DNA
<213> ORGANISM: Artificial Sequence
<220> FEATURE:
<223> OTHER INFORMATION: SYNTHESIZED

<400> SEQUENCE: 4
ctgcacctgg cctaggaact gctataatgc cttgacctaa ggcaggataa atcagg      56
```

```
<210> SEQ ID NO 5
<211> LENGTH: 60
<212> TYPE: DNA
<213> ORGANISM: Artificial Sequence
<220> FEATURE:
<223> OTHER INFORMATION: SYNTHESIZED

<400> SEQUENCE: 5
cactatagaa ctcgagtttt ttcaaatatt tataaaaaca ggaaaaaaga agaaaaaata      60

<210> SEQ ID NO 6
<211> LENGTH: 60
<212> TYPE: DNA
<213> ORGANISM: Artificial Sequence
<220> FEATURE:
<223> OTHER INFORMATION: SYNTHESIZED

<400> SEQUENCE: 6
ctgcacctgg cctaggataa catttacaat ccttattatt attattatta ttgttgatgg      60

<210> SEQ ID NO 7
<211> LENGTH: 53
<212> TYPE: DNA
<213> ORGANISM: Artificial Sequence
<220> FEATURE:
<223> OTHER INFORMATION: SYNTHESIZED

<400> SEQUENCE: 7
cactatagaa ctcgagatgt aaaatcaga tgtagtgctt ttattgtata tac              53

<210> SEQ ID NO 8
<211> LENGTH: 58
<212> TYPE: DNA
<213> ORGANISM: Artificial Sequence
<220> FEATURE:
<223> OTHER INFORMATION: SYNTHESIZED

<400> SEQUENCE: 8
ctgcacctgg cctaggtaga gttaattcta tattaaaatt attatttgaa ttatcatc        58
```

COMBINATION ARTEMISININ AND CHEMILUMINESCENT PHOTODYNAMIC THERAPY AND USES THEREFOR

CROSS REFERENCE TO RELATED APPLICATIONS

This application claims the benefit of U.S. Provisional Application No. 62/183,042, filed Jun. 22, 2015, each of the disclosures of which is hereby incorporated by reference in its entirety.

GOVERNMENTAL RIGHTS

This invention was made with government support under R21-AI110712 awarded by the United States National Institutes of Health. The government has certain rights in the invention.

FIELD OF THE INVENTION

Photodynamic therapy-based methods of treating diseases such as cancer and malaria are disclosed. These methods include administering 5-aminolevulinic acid (ALA), luminol and artemisinin (ART). ART and ALA administered in combination with luminol can kill malaria parasites without host toxicity. In some aspects, the methods further include administration of a luminol enhancer such as 4-iodophenol. The disclosed methods can also be used to remove potential malaria pathogens from the blood supply.

BACKGROUND OF THE INVENTION

Photodynamic therapy (PDT) is a method of treating cancer that utilizes a photoreactive chemical, referred to as a photosensitizer, to create a reactive molecule that confers cytotoxicity. In many forms, the photosensitizer can create a reactive oxygen species which can be cytotoxic. Photosensitizers can include many forms of photoreactive chemicals such as p-phenylene vinylene. Specific cells such as cancer cells can be targeted using targeted light sources. Light can be produced from outside sources, or from chemiluminescent sources such as luminol, which must become activated in order to produce light.

Photodynamic therapy is a method of leveraging metabolic synthesis of 5-aminolevulinic acid (ALA) into protoporphyrin IX (PPIX) which is a precursor to heme synthesis (Celli et al. *Chem. Rev.* 2010, 110, 2795-2838). Heme is a ubiquitous biological cofactor required by nearly all organisms to carry out diverse redox biochemistry (Ponka, P., *Am. J. Med. Sci.* 318, 241-256, 1999). Heme metabolism is a dominant feature of *Plasmodium* infection of erythrocytes, the most heme-rich cell in the human body and the stage of parasite development that causes all clinical symptoms of malaria. Parasites sequester and biomineralize the copious heme released during large-scale hemoglobin digestion in their acidic food vacuole, but they also require heme as a metabolic cofactor for cytochrome-mediated electron transfer within mitochondria (Sigala and Goldberg, *Ann. Rev. Microbiol.* 68, 259-278, 2014).

Malaria is an ancient and deadly disease, with hundreds of millions of people infected by *Plasmodium malaria* parasites and more than half a million deaths each year.

Progress has been made in reducing the global malaria burden, due in part to the success of artemisinin (ART)-based combination drug therapies (ACTs). ART is an antimalarial drug that also shows anti-cancer properties. ART contains an endoperoxide moiety thought to be activated in vivo via interactions with reduced iron (e.g. heme) and, without being limited by theory, is believed to exert its antimalarial and anti-cancer effects by generating cytotoxic oxygen radicals. Recent identification of artemisinin-tolerant parasites in southeast Asia, however, has raised concerns that the broad potency of ACT's against all parasite strains may be losing efficacy, which could lead to a resurgence in malaria deaths (Ariey, F., et al., *Nature* 505, 50-55, 2014).

ART has also been shown in vitro to be a potent activator of chemiluminescence by luminol. U.S. Pat. No. 8,603,985 to Weissbach et al. discloses the use of ART as an anti-cancer agent. However, this reference does not disclose the use of ART in PDT, only as a chemical agent.

Laptev, R., et al., *British J. Cancer* 95, 189-196, 2006 describes the use of bioconjugates transferrin and haematoporphyrin as a luminol activator; this reference does not disclose the use of ALA or artemisinin (ART). Yuan, H., et al., *J. Am. Chem. Soc.* 134, 13184-13187, 2012, describes a photodynamic therapy technique that uses chemiluminescent luminol as the light source instead of an external light source in order to allow penetration of deeper tissues; p-phenylene vinylene is used as the photosensitizer instead of ALA. Chen, T.-C., et al., (*Process Biochemistry* 47, 1903-1908, 2012) describes the use of luminol as a light source with ALA as the photosensitizer. This reference does not describe the use of ART.

Li, Y. J., et al., *Cell Physiol. Biochem.* 33, 1527-1536, 2014, treated cultured esophageal cancer cells with 5-ALA and dihydroartemisinin—a derivative of ART. However, this reference does not discuss the use of luminol or CL to activate ALA.

Zhang, S. and Gherhard, G. S., *PLoS One* October 28; 4(10), e7472, 2009, discloses methods of testing cytotoxicity of ART and ALA as chemical compositions, but does not disclose methods of photodynamic therapy, radiation and chemicals, or CL.

US patent application publication 20130108710 of Tanaka et al. discloses the use of ALA as a malaria drug in conjunction with other, known malaria drugs such as ART. However, this reference reports that the concentration of ALA required to kill malaria parasites is also toxic to humans. There is no disclosure or suggestion of using a combination of ALA and ART in photodynamic therapy.

Baptista, M. S. and Wainwright, M., *Brazilian J. Med. Biol. Res.* 44, 1-10, 2011, propose the use of PDT as a treatment for malaria, but note that "the light requirement means that the treatment of disseminated diseases is not feasible at present."

FIG. 1A is a schematic depiction of the heme biosynthesis pathway in *P. falciparum* parasites. Enzymes abbreviations are in red and pathway substrates and intermediates are in black: ALAS (aminolevulinic acid synthase), ALAD (aminolevulinic acid dehydratase), PBGD (porphobilinogen deaminase), UROS (uroporphyrinogen synthase), UROD (uroporphyrinogen decarboxylase), CPO (coproporphyrinogen III oxidase), PPO (protoporphyrinogen IX oxidase), FC (ferrochelatase). For simplicity, all organelles are depicted with single membranes. This pathway was originally proposed to be essential for blood-stage parasite development and thus a potential drug target (Surolia, N. and Padmanaban, G., *Biochem. Biophys. Res. Commun.* 187, 744-750, 1992). Recent studies, however, have clarified that de novo heme synthesis is not required by intraerythrocytic parasites and thus is not a viable target for therapeutic inhibition (Ke, H., et al., *J. Biol. Chem.* 289, 34827-34837, 2014; Nagaraj, V. A., et al. *PLoS Pathogens* 9, e1003522, 2013).

Conventional PDT requires an external light source to illuminate and selectively kill ALA-stimulated cells (Celli, J. P. et al., *Chem. Rev.* 110, 2795-2838, 2010). While such approaches can successfully target localized shallow-tissue tumors, they are impractical for treating malaria due to the dispersed nature of blood-stage infection and the requirement to illuminate every infected erythrocyte. To bypass the need for external light, chemiluminescence has been proposed as an alternative means to photoactivate the cytotoxicity of PPIX in ALA-stimulated cells. Trial studies in cancer cells lines have shown modest success using the small molecule luminol (Chen, T-C., et al., *Process Biochem.* 47, 1903-1908, 2012; Laptev, R. et al., *Br. J. Cancer* 95, 189-196, 2006), whose iron-activated chemiluminescence overlaps the excitation spectrum of PPIX (Rose, A. L., et al., *Analytical Chemistry* 73, 5909-5920, 2001).

Production of aminolevulinic acid (ALA) catalyzed by ALA synthase (ALAS) is the rate-limiting step in heme biosynthesis. Exogenous ALA bypasses this regulated step and stimulates biosynthetic flux, leading to accumulation of the final intermediate, protoporphyrin IX (PPIX), and conversion of PPIX to heme by ferrochelatase becomes the new rate-limiting step (Kennedy, J. C., et al. *J. Photoch. Photobio.* B 6, 143-148, 1990). Since PPIX is fluorescent (FIG. 1B), cellular accumulation of PPIX can be directly visualized by fluorescence microscopy (Celli, J. P., et al., *Chem. Rev.* 110, 2795-2838, 2010). PPIX is also known to generate cytotoxic reactive oxygen species (ROS) when photo-illuminated. The ability to kill ALA-treated cells by light activation of accumulating PPIX has been exploited to selectively target cancerous tumors via a strategy known as photodynamic therapy (Celli, J. P., et al., *Chem. Rev.* 110, 2795-2838, 2010).

SUMMARY OF THE INVENTION

The present inventors have developed photodynamic therapies involving ALA-stimulating production of a phototoxic compound, protoporphyrin IX (PPIX), and activation of PPIX cytotoxicity in situ within infected erythrocytes. In various embodiments, PPIX cytotoxicity can be effected by using low-dose artemisinin to stimulate chemiluminescence of luminol. Methods of the present teachings can be used to treat various diseases, including, without limitation malaria and cancer. Methods of the present teachings can also be used to remove potential malaria pathogens from the blood supply.

In various embodiments, methods of the present teachings can comprise administration of 5-aminolevulinic acid (ALA) or a derivative thereof, luminol and artemisinin (ART) or a derivative thereof in therapeutically effective amounts. Non-limiting examples of derivatives of ALA may be as disclosed in US 2013/0108710 and Fotinos et al. *Photochemistry and Photobiology* 2006; 82(4): 994-1015. These methods can further comprise administration of a luminol enhancer such as, without limitation, 4-iodophenol (Kamidate, T., et al., *Anal. Sci.* 25, 1163-1166, 2009). Other luminol enhancers can include p-phenylphenol, 1,6-dibromonaphth-2-ol, p-hydroxycinnamic acid, 1-bromonaphth-2-ol, 6-hydroxybenzothiazole, p-bromophenol, p-chlorophenol, 2-chloro-4-bromophenol, 2,4-dichlorophenol, 3,4-dichlorophenol, and those described in Thorpe et al. *Methods of Enzymology* 1986, 133: 331-353, the disclosure of which is hereby incorporated by reference in its entirety. In some embodiments, methods of the present teachings can comprise administration of ALA and luminol, with or without 4-iodophenol, in therapeutically effective amounts. In some embodiments, these methods can be used in the treatment of cancer. In some embodiments, these methods can be used in the treatment of malaria. In some embodiments, these methods can be used to clean the blood supply of potential malaria pathogens.

In an aspect, the disclosure provides a method of treating malaria, comprising administering to a subject in need thereof, therapeutically effective amounts of: 5-aminolevulinic acid; luminol; and artemisinin. The method can further comprise administering a therapeutically effect amount of 4-iodophenol.

In another aspect, the disclosure provides a method of treating cancer, comprising administering to a subject in need thereof, therapeutically effective amounts of: 5-aminolevulinic acid; luminol; and artemisinin. The method can further comprise administering a therapeutically effect amount of 4-iodophenol.

In still another aspect, the disclosure provides a method of killing intraerythrocytic parasites, the method comprising contacting the parasites with therapeutically effective amounts of: 5-aminolevulinic acid or a derivative thereof; luminol or a derivative thereof; and artemisinin or a derivative thereof. In an embodiment, the method further comprises administering a therapeutically effective amount of 4-iodophenol. In another embodiment, the artemisinin or derivative thereof is selected from the group consisting of artemisinin, artesunate, artemether, dihydroartesmisinin, artelinic acid, and artemotil. In still another embodiment, the artemisinin or derivative thereof is dihydroartesmisinin. In still yet another embodiment, the artemisinin or derivative thereof is administered at a sub-therapeutic dose. In other embodiments, the sub-therapeutic dose is ≤10% of the $EC_{50}$ of the artemisinin or derivative thereof. In some embodiments, the luminol or derivative thereof is selected from the group consisting of lumino, luminol sodium salt, luminol hemihydrate, luminol hydrochloride, isoluminol, isoluminol monohydrate, and isoluminol ABEI. In different embodiments, the 5-aminolevulinic acid or derivative thereof is selected from the group consisting of 5-aminolevulinic acid (5-ALA), methylaminolevulinate, hexylaminolevulinate, 5-ALA esters, and 5-ALA amides. In certain embodiments, the killing of intraerythrocytic parasites is indicative by pyknosis. In some embodiments, the parasites are malarial parasites. In specific embodiments, the parasites are *Plasmodium falciparum*. In an embodiment, the parasites are drug-resistant. Specifically, the parasites are artemisinin-resistant.

In still yet another aspect, the disclosure provides a method of treating blood-stage malaria, the method comprising administering to a subject in need thereof, therapeutically effective amounts of: 5-aminolevulinic acid or a derivative thereof; luminol or a derivative thereof; and artemisinin or a derivative thereof. In an embodiment, the method further comprises administering a therapeutically effective amount of 4-iodophenol. In another embodiment, the artemisinin or derivative thereof is selected form the group consisting of artemisinin, artesunate, artemether, dihydroartesmisinin, artelinic acid, and artemotil. In still another embodiment, the artemisinin or derivative thereof is administered at a sub-therapeutic dose. In still yet another embodiment, the luminol or derivative thereof is selected from the group consisting of lumino, luminol sodium salt, luminol hemihydrate, luminol hydrochloride, isoluminol, isoluminol monohydrate, and isoluminol ABEI. In a different embodiment, the 5-aminolevulinic acid or derivative thereof is selected from the group consisting of 5-aminolevulinic acid (5-ALA), methylaminolevulinate, hexylaminolevulinate, 5-ALA esters, and 5-ALA amides. In other embodiments, the parasites are artemisinin-resistant.

BRIEF DESCRIPTION OF THE FIGURES

The application file contains at least one drawing executed in color. Copies of this patent application publication with color drawing(s) will be provided by the Office upon request and payment of the necessary fee.

DETAILED DESCRIPTION OF THE INVENTION

Figure 1A:
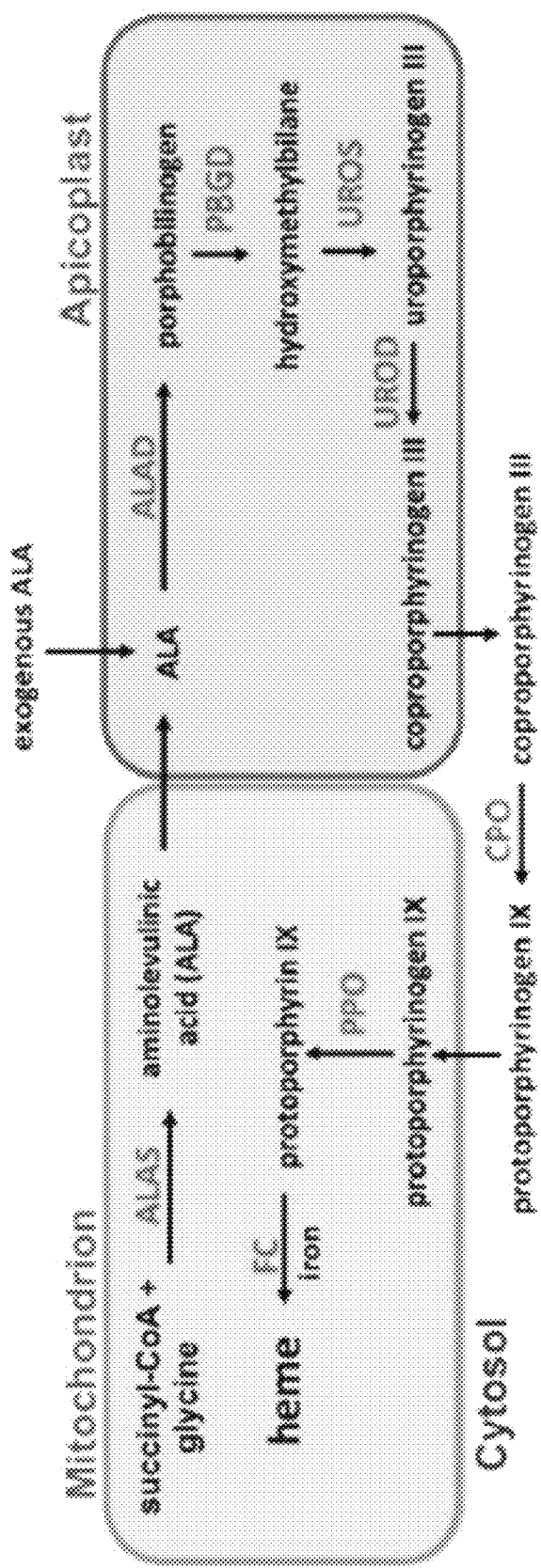
FIG. 1A illustrates a schematic representation of heme synthesis and FIG. 1B illustrates the spectrographic analysis of PPIX.
Figure 1B:
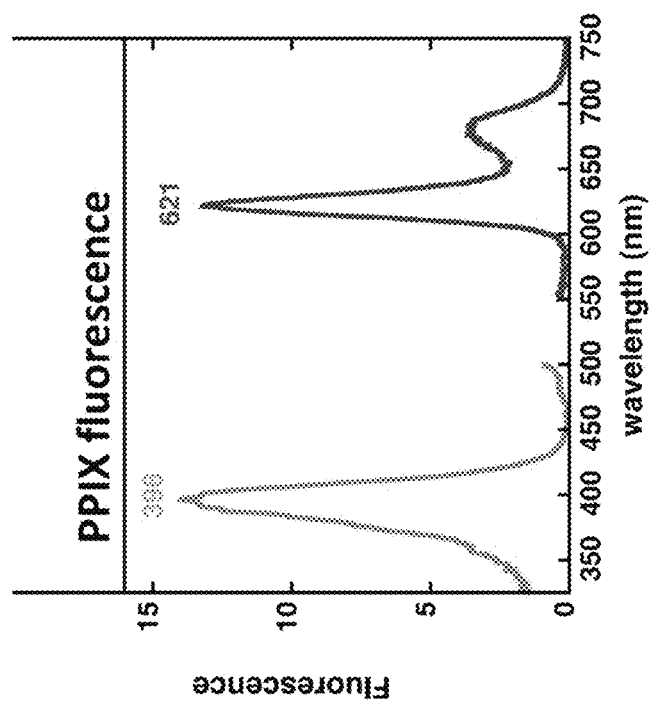

The present inventors describe methods of photodynamic therapy for use against diseases, such as and without limitation, cancer and malaria. In various embodiments, the photosensitizer can be 5-aminolevulinic acid. In some embodiments, photodynamic therapy can comprise administration of artemisinin (ART) or a therapeutically acceptable salt or derivative thereof, luminol and 5-aminolevulinic acid (ALA) for chemiluminescence therapy. In some embodiments, 4-iodophenol can be administered in addition to ART, luminol and ALA. Without being limited by theory, treatment with ALA, a heme biosynthesis intermediate, can lead to cellular accumulation of protoporphyrin IX (PPIX). In turn, PPIX can generate cytotoxic oxygen radicals when illuminated. In various configurations, illumination can be from an external light source or light from a chemiluminescent compound. In various embodiments, the present teachings include the use of ALA treatment as a photosensitizer, luminol as the CL agent, and ART as the activator of chemiluminescence by luminol, without or with the enhancer 4-iodophenol. In various configurations, methods of the present teachings can be used to treat malaria, clean ex vivo blood of malaria parasites, or to treat cancer.

The present inventors disclose photodynamic treatment strategies that include photosensitizing *Plasmodium* parasites with ALA and then killing them with light. The present inventors have developed treatment methods which, in various embodiments, can circumvent conventional PDT requirements for external light and can ablate parasite growth. In various configurations, these methods can include luminol-based chemiluminescence, stimulated by combinatorial delivery of artemisinin, e.g., low-dose artemisinin. In various embodiments, these methods can include administration of ALA, luminol and artemisinin (or a clinical derivative) for treating malaria. In various configurations, multidrug-resistant parasites can remain susceptible to this photodynamic strategy. In some configurations, a photodynamic strategy disclosed by the inventors can have an additional advantage of exploiting host enzyme activity refractory to development of resistance-conferring mutations.

In various embodiments, the use of artemisinin to stimulate intracellular light emission by luminol for ALA-based photodynamic therapy can be applicable to treatment of a deep-tissue cancer. In some configurations of the present teachings, such as when poor accessibility to external light can limit current PDT approaches for cancer therapy, artemisinin (ART) administration in combination with ALA and luminol can synergistically provide cancer chemotherapy which can be unexpectedly powerful in its beneficial effects.

Abbreviations:
ALA aminolevulinic acid
ALAD ALA dehydratase
ALAS ALA synthase
ART artemisinin
CL-PDT chemiluminescence-based photodynamic therapy
cobA uroporphyrinogen III methyltransferase
CPO coproporphyrinogen III oxidase
DDD DHFR degradation domain
DHA dihydroartemisinin
FC ferrochelatase
IPP isopentenyl pyrophosphate
NPP new permeability pathways
PBGD porphobilinogen deaminase
PDT Photodynamic therapy
PPIX protoporphyrin IX
TMP trimethoprim
Methods The methods and compositions described herein utilize laboratory techniques well known to skilled artisans, and can be found in laboratory manuals such as Sambrook, J., et al., Molecular Cloning: A Laboratory Manual, 3rd ed. Cold Spring Harbor Laboratory Press, Cold Spring Harbor, N.Y., 2001; Spector, D. L. et al., Cells: A Laboratory Manual, Cold Spring Harbor Laboratory Press, Cold Spring Harbor, N.Y., 1998; Nagy, A., Manipulating the Mouse Embryo: A Laboratory Manual (Third Edition), Cold Spring Harbor, N.Y., 2003; Harlow, E., Using Antibodies: A Laboratory Manual, Cold Spring Harbor Laboratory Press, Cold Spring Harbor, N.Y., 1999; and Carruthers, W., and Coldham, I., Modern Methods of Organic Synthesis (4th Edition), Cambridge University Press, Cambridge, U.K., 2004. Methods of administration of pharmaceuticals and dosage regimes, can be determined according to standard principles of pharmacology well known skilled artisans, using methods provided by standard reference texts such as Remington: the Science and Practice of Pharmacy (Alfonso R. Gennaro ed. 19th ed. 1995); Hardman, J. G., et al., Goodman & Gilman's The Pharmacological Basis of Therapeutics, Ninth Edition, McGraw-Hill, 1996; and Rowe, R. C., et al., Handbook of Pharmaceutical Excipients, Fourth Edition, Pharmaceutical Press, 2003. As used in the present description and the appended claims, the singular forms "a", "an" and "the" are intended to include the plural forms as well, unless the context indicates otherwise. All publications cited herein are hereby incorporated by reference, each in their entirety.

Materials

All reagents were of the highest purity commercially available. Succinylacetone, 5-aminolevulinic acid, trimethoprim, furosemide, saponin, isopentenyl pyrophosphate, doxycycline, luminol, and dihydroartemisinin were purchased from Sigma-Aldrich Co., St. Louis, Mo. 5-[$^{13}$C4] aminolevulinic acid and $^{13}$C2-glycine were purchased from Cambridge Isotope Laboratories, Inc., Tewksbury, Mass.

Microscopy

Images of live or fixed parasites were acquired on an Axio Imager.M1 epifluorescence microscope (Carl Zeiss Microimaging, Inc.) equipped with a Hamamatsu ORCA-ER digital CCD camera and running Axiovision 4.8 software, as described previously (Sigala, P. A., et al., *J. Biol. Chem.* 287, 37793-37807, 2012). Live parasite nuclei were stained with 5 µM Hoechst 33342 added immediately prior to image acquisition. For photodynamic imaging studies, parasites were cultured in 200-500 µM ALA in the absence or presence of 50 µM succinylacetone for 6-12 hours prior to visualization. Hemozoin movement in parasite digestive vacuoles were imaged by acquiring 10-20 sequential frames at 1 second intervals on the bright-field channel. Images were cropped and superimposed in Adobe Photoshop and exported as movie files with a 0.1 second frame delay. Immunofluorescence images were acquired by fixing and staining parasites as previously described (Tonkin, C. J., et al., *Mol. Biochem. Parasitol* 137, 13-21, 2004; Ponpuak, M., et al., *Mol. Microbiol.* 63, 314-334, 2007). Electron microscopy images were obtained as previously described (Beck, J. R., et al., *Nature* 511, 592-595, 2014). Uninfected erythrocytes were washed and resuspended in 1× cytomix (120 mM KCl (anhydr); 0.15 mM CaCl2; 10 mM KH2PO4 (anhydr); 25 mM HEPES; 2 mM EGTA; 5 mM MgCl2; Adjust pH to 7.6 with KOH) containing 500 µM ALA, electroporated in a manner identical to parasite transfections (see below), washed in PBS, incubated overnight at 37° C., and imaged as described above for live parasites. Images acquired on different channels for common samples were processed with identical brightness and contrast settings.

Parasite Growth Analysis

Parasite growth was monitored by diluting asynchronous parasites to 0.5% parasitemia and allowing culture expansion with daily or twice daily media changes. Parasitemia was measured daily by diluting 10 µl of each resuspended culture in 200 µl acridine orange (1.5 µg/ml) and analyzing by flow cytometry, as previously described (Muralidharan, V., et al., *Nat. Commun.* 3, 1310, 2012). To assess the light sensitivity of ALA-treated parasites, asynchronous parasites were cultured in 200-500 µM ALA in the absence or presence of 50 µM succinylacetone and subjected to 2-5 minute daily exposures to broad wavelength white light on an overhead projector. Daily parasitemia measurements were plotted as a function of time and fit to an exponential growth equation using Graph Pad Prism 5.0 (Graph Pad Software, Inc., La Jolla, Calif.).

For chemiluminescence experiments, asynchronous parasites were diluted to 0.5% parasitemia and incubated ±50-100 µM ALA and ±50 µM succinylacetone for 8 hours. After 8 hours, parasite media was changed to also include 750 µM luminol and 500 pM dihydroartemisinin in the indicated combinations. Parasite cultures were allowed to expand over 5 days, with twice-daily (7 am and 4 pm) media changes in the indicated combinations. Parasitemia was measured daily as indicated above. Experiments were performed using 3D7 (drug sensitive) parasites, Dd2 (multidrug resistant) parasites (Sidhu, A. B. S., et al., *Science* 298, 210-213, 2002), and a clinical isolate (MRA-1241; Ariey, F. et al., *Nature* 505, 50-55, 2014) bearing the I543T mutation in the Kelch-13 gene locus.

Parasite Strains, Culture, Genetic Modification, and Transgene Expression

Parasite culture and transfection were performed as previously described (Sigala, P. A., et al., *J. Biol. Chem.* 287, 37793-37807, 2012). Cloning was performed using either restriction endonuclease digestion and ligation or the In-Fusion system (Clontech Laboratories, Inc., Mountain View, Calif.).

For episomal expression of *P. falciparum* ALA dehydratase (PF3D7_1440300) fused to a C-terminal GFP tag, cDNA encoding the complete ALAD gene (exons only) was RT-PCR amplified from total parasite RNA using the Superscript III system (Life Technologies, Grand Island, N.Y.) and primers 5'-CACTATAGAACTCGAGATGTTAAAATCA-GATGTAGTGCTTTTATTGTATATAC-3' (SEQ ID NO:7) and 5'-CTGCACCTGGCCTAGGTAGAGTTAATTCTAT-ATTAAAATTATTATTTGAATTATCATC-3' (SEQ ID NO:8), digested with XhoI/AvrII, and ligated into the XhoI/AvrII sites of a digested pTEOE vector that was identical to a previously described pTyEOE vector (Beck, J. R., et al., *Nature* 511, 592-595, 2014) except that the pTEOE plasmid contained human DHFR in place of yeast DHOD as the positive selection marker. Plasmid-based expression of the ALAD-GFP fusion was driven by the HSP86 promoter. This plasmid (50 µg) was co-transfected into 3D7 parasites along with plasmid pHTH (10 µg) for transient expression of the piggyback transposase that mediates integration of the pTEOE plasmid into the parasite genome (Balu, B., et al., *Proc. Nat'l Acad. Sci. USA* 102, 16391-16396, 2005). Parasites were selected (Mamoun, C. B., et al., *Proc. Nat'l. Acad. Sci. USA* 96, 8716-8720, 1999) with 5 nM WR.

For episomal expression of *Propionibacterium freudenreichii* (*shermanii*) uroporphyrinogen III methyltransferase (cobA) (Genbank: CBL55989.1) targeted to the parasite apicoplast, the cobA gene was PCR-amplified from plasmid pISA41728 using the primers 5'-ACGAT-TTTTTCTCGAGATGACCACCACACTGTTGCC-CGGCACTGTC-3' (SEQ ID NO: 1) and 5'-CTGCACCTGGCCTAGGGTGGTCGCTGGGCGCGC-GATGG-3'(SEQ ID NO: 2), digested with XhoI/AvrII, and ligated into the XhoI/AvrII-cut pTEOE vector described above. An insert encoding the *P. falciparum* acyl carrier protein (ACP) leader sequence (residues 1-60) with 5'- and 3'-XhoI sites, previously PCR-amplified from parasite cDNA, 42 was digested with XhoI and ligated into the XhoI-cut cobA/pTEOE vector to generate an in-frame ACPL-cobA-GFP fusion gene. This plasmid was co-transfected with pHTH into 3D7 parasites as described above.

For disruption of the *P. falciparum* genes encoding PBGD (PF3D7_1209600) and CPO (PF3D7_1142400), primer pairs (PBGD: 5'-CACTATAGAACTCGAGGATCAT-AATAATGATACATTATGTACTATTGGGACATCGTCC-3' (SEQ ID NO: 3) and 5'-CTGCACCTGGCCTAG-GAACTGCTATAATGCCTTGACCTAAGGCAGGATAA-ATCAGG-3' (SEQ ID NO: 4); CPO: 5'-CAC-TATAGAACTCGAGTTTTTTCAAATATTTATAAAAA-CAGGAAAAAAGAAGAAAAAATA-3' (SEQ ID NO: 5) and 5'-CTGCACCTGGCCTAGGATAACATTTACAATC-CTTATTATTATTATTATTATTGTTGATGG-3' (SEQ ID NO: 6)) were used to PCR-amplify 360 bp and 471 bp sequences from the middle of the 1.3 kb PBGD and 1.6 kb CPO genes, respectively. These inserts were cloned by IN-FUSION® (PCR based cloning) into the XhoI/AvrII sites of the pPM2GT vector (Klemba et al. 2004 *J. Cell Biol.* 164, 47-56), which contains a human DHFR marker for positive selection with 5 nM WR, and plasmids (50 μg) were transfected into 3D7 parasites by electroporation. Parasites were subjected to three rounds of positive selection with 5 nM WR, with the first and second selections followed by three-week periods of maintenance in the absence of drug pressure. After the third round of positive selection, parasites were cloned by limiting dilution. Clonal parasites that had integrated the plasmid at the desired locus to disrupt the target genes by single crossover homologous recombination were verified by PCR and southern blot, as previously described (Klemba, M., et al., *J. Cell Biol.* 164, 47-56, 2004), and retained for further analysis.

For apicoplast disruption experiments, parasites were cultured in 1 jiM doxycycline and 200 μM IPP for 7-21 days. After 7 days, genomic DNA was harvested and analyzed by PCR to confirm selective loss of the apicoplast genome.

Analysis of Heme Biosynthesis by $^{13}$C-Labeling and Tandem Mass Spectrometry

Parasites were cultured in 200 μM 5-[$^{13}$C4]-ALA for 12-24 hours, harvested by centrifugation, lysed in 0.05% cold saponin, washed in PBS, and extracted with DMSO. Deuteroporphyrin was added as an internal standard, and extracts were analyzed for $^{13}$C-labeled heme, PPIX, and CPPIII using a previously published liquid chromatography-multiple reaction monitoring tandem mass spectrometry assay (Ke, H. et al., *J. Biol. Chem.* 289, 34827-34837, 2014).

Fractionation of Parasite-Infected Erythrocytes

To assess whether parasites could synthesize heme from ALA in the absence of host enzymes in the erythrocyte cytoplasm, parasite-infected red blood cells were lysed with 0.05% saponin (0.2 μM filtered), spun briefly and gently to pellet, washed in PBS, and resuspended in 12 ml of RPMI/Albumax® (Life Technologies, Grand Island, N.Y.), growth media supplemented with 200 μM 5-[$^{13}$C4]-ALA. Parasites were incubated overnight at 37° C., harvested by centrifugation, and extracted and analyzed by tandem mass spectrometry as described above.

Preparation of Lysates from Uninfected Erythrocytes

To assess the heme biosynthesis capacity of the erythrocyte cytoplasm, 500 μl packed red blood cells (described previously; Sigala, P. A., et al., *J. Biol. Chem.* 287, 37793-37807, 2012) were lysed in 20 ml of 0.04% saponin/PBS (0.2 μM filtered) and centrifuged at 25,000×g for 60 minutes to pellet unlysed cells and any organelles. The superficial 15 ml of the lysate supernatant was removed and 0.2 μM filtered, supplemented with 200 μM 5-[$^{13}$C4]-ALA in the absence or presence of 50 μM succinylacetone, incubated overnight at 37° C., and analyzed by tandem mass spectrometry as described above.

Chemical Block of Parasite Nutrient Uptake Pathways

The 3D7 parasite line expressing the endogenous HSP101 from its genomic locus and bearing a C-terminal *E. coli* DHFR degradation domain (DDD) fusion tag was previously published (Beck, J. R., et al., *Nature* 511, 592-595, 2014). To test whether ALA-uptake by parasite infected erythrocytes depends on parasite-established nutrient acquisition pathways in the host cell membrane, the inventors split a synchronous culture of HSP101-DDD into two populations of late schizonts (purified over a magnetic column) and washed out trimethoprim (TMP) from one of the two cultures. Both cultures (±TMP) were permitted to lyse and reinvade fresh erythrocytes overnight. The following morning, parasites were placed in 200 μM ALA as early rings, incubated for 8 hours at 37° C., and imaged by live parasite microscopy as described above. Alternatively, asynchronous wild-type 3D7 parasites were incubated in the absence or presence of 100 μM furosemide for one hour to block nutrient acquisition pathways, followed by addition of 500 μM ALA and further incubation for eight hours. Parasites were then imaged by live parasite microscopy as described above.

Antibodies

The following antibodies were used for immunofluorescence (IFM) and western blot (WB) analysis at the indicated dilutions: goat anti-GFP (Abcam 5450, Abcam, Cambridge, Mass.) (IFM 1:500, WB 1:1000), rabbit anti-ACP44,48 (IFM: 1:500), ALEXA FLUOR® 488-conjugated chicken anti-goat (IFM: 1:500), ALEXA FLUOR® 555-conjugated donkey anti-rabbit (Life Technologies, Grand Island, N.Y.) (IFM: 1:500), donkey anti-goat-IRDye 800 (Licor Biosciences, Lincoln, Nebr.) (WB: 1:10,000).

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Figure 2:
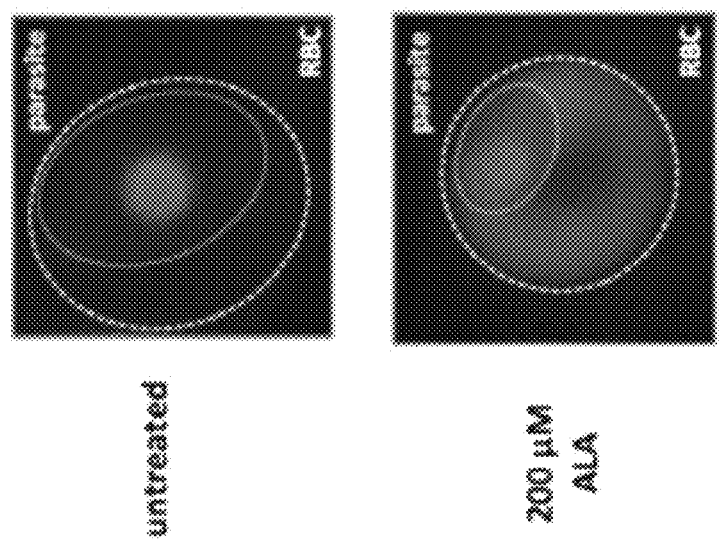
FIG. 2 illustrates parasite growth in the presence or absence of ALA.

Example 1. Exogenous ALA can be Used to Stimulate Heme Biosynthesis and Photosensitize Parasites The present inventors investigated whether ALA treatment could serve as a probe of heme biosynthesis activity in Plasmodium-infected erythrocytes by enabling direct visualization of PPIX production and the cellular consequences of light activation. Untreated parasites imaged on an epifluorescence microscope display only background auto-fluorescence from hemozoin crystals in the parasite digestive vacuole (FIG. 2). Parasites grown in 200 μM ALA, however, display bright red fluorescence distributed throughout the infected erythrocyte, as expected for accumulation of PPIX (additional discussion below).

Figure 3A:
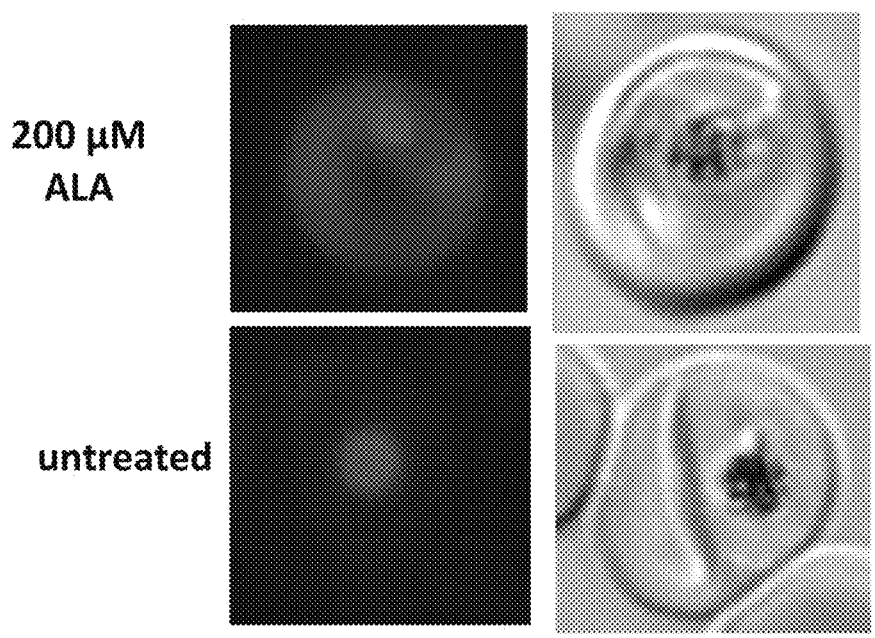
FIG. 3A and FIG. 3B illustrate that hemozoin dynamics in ALA-treated parasites can be rapidly ablated by light.
Figure 3B:
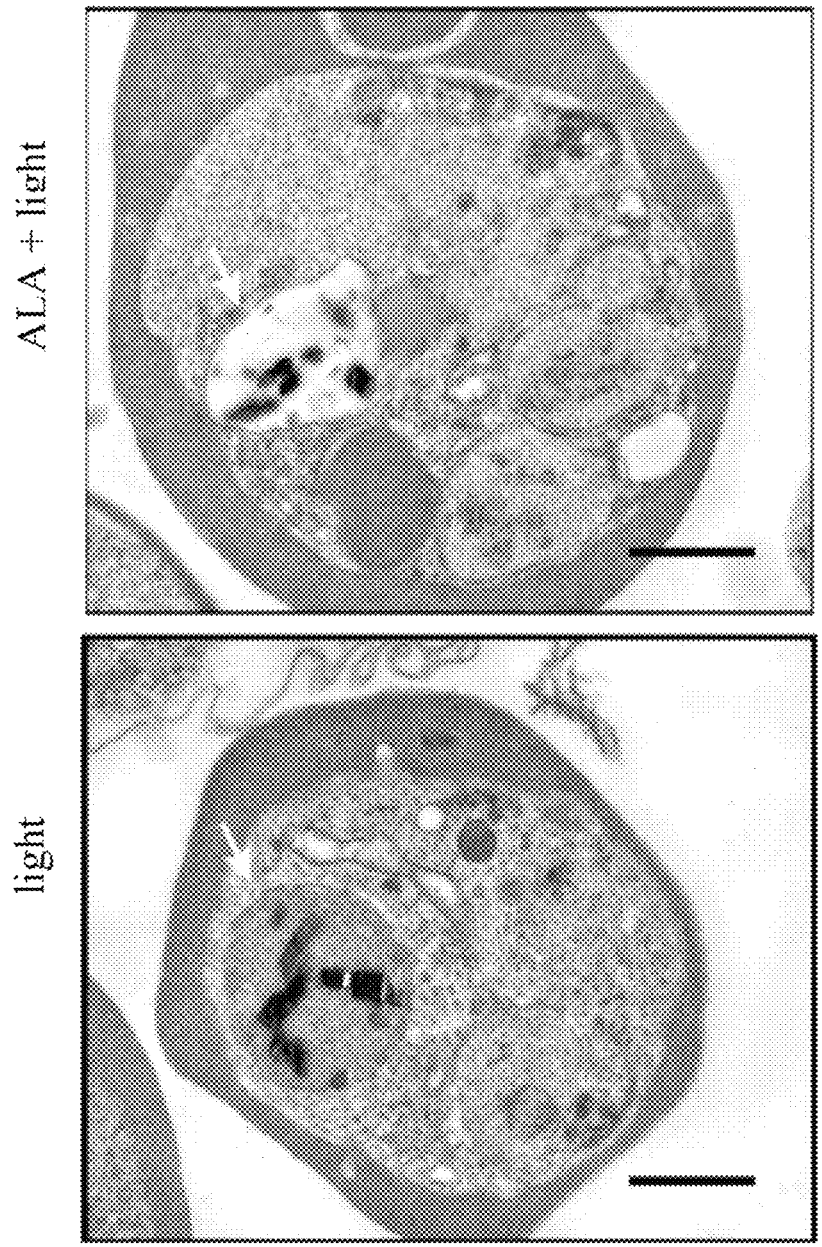

The cytotoxic effects of light-activating PPIX were readily apparent by monitoring the motion of hemozoin crystals that dynamically tumble within the digestive vacuole of individual parasites. Although the origin and physiological significance of this motion remain unknown, hemozoin dynamics serve as an internal biomarker of food vacuole integrity and parasite viability (Sigala, P. A. and Goldberg, D. E., *Annu. Rev. Microbiol.* 68, 259-278, 2014). Hemozoin motion in untreated parasites is unaffected by a several second acquisition of a fluorescent image whose excitation wavelength overlaps that of PPIX. In contrast, the hemozoin dynamics in ALA-treated parasites are rapidly ablated by light (FIG. 3A). FIG. 3A depicts bright field and fluorescence microscopy images of untreated and 200 μM ALA-treated parasites. Fluorescence images were acquired with a Zeiss filter set 43 HE (excitation 537-562 nm, emission 570-640 nm). Ultrastructural analysis by electron microscopy revealed a loss of electron density within the digestive vacuole of ALA-treated and illuminated parasites, illustrating disruption of the food vacuole membrane and outward diffusion of the vacuolar protein contents. FIG. 3B depicts Transmission electron microscopy images of untreated (left)

and 500 µM ALA-treated (right) *P. falciparum*-infected erythrocytes after light exposure on an overhead projector lightbox. The white arrow identifies the digestive vacuole. Scale bar equals 1 µm. These changes indicate a photodynamic mechanism of PPIX-mediated generation of reactive oxygen species that lead to pleiotropic cytotoxic damage, including loss of lipid bilayer integrity.

Figure 4:
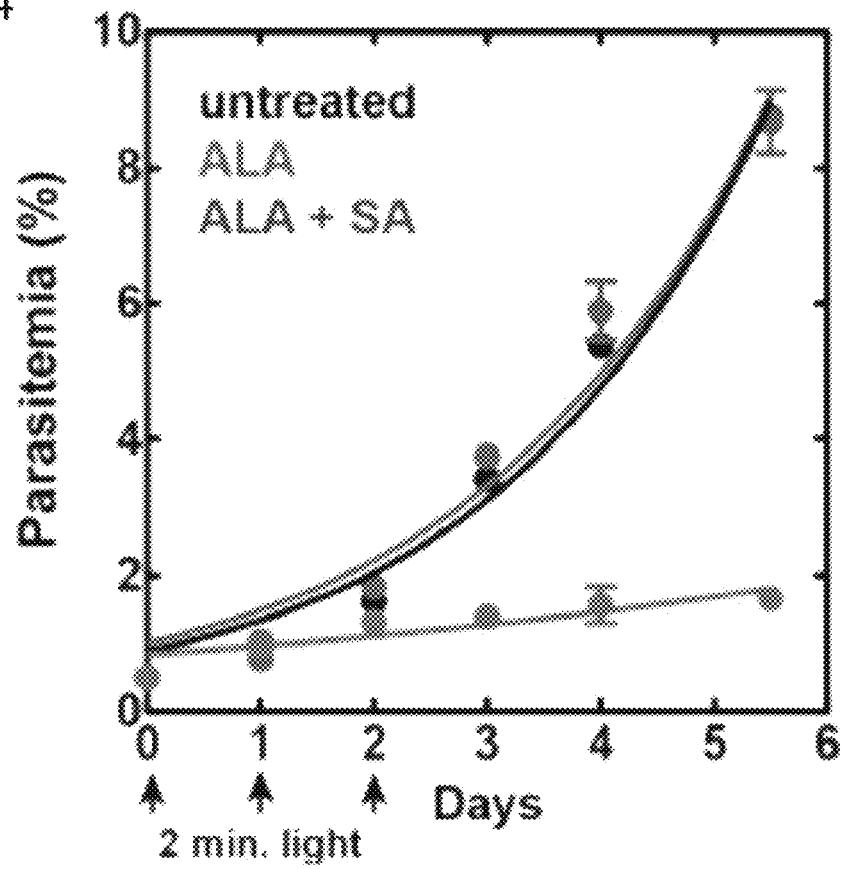
FIG. 4 illustrates the growth of untreated versus ALA-treated parasites over several days with 2-minute daily exposures to broad-wavelength white light on an overhead projector light box.

To test the effects of these changes on bulk parasite culture, the present inventors monitored the growth of untreated versus ALA-treated parasites over several days with 2-minute daily exposures to broad-wavelength white light on an overhead projector light box. FIG. 4 depicts growth of asynchronous 3D7 parasites in the presence or absence of 200 µM ALA and 50 µM succinylacetone (SA), with 2-minute exposures to white light on an overhead projector on days 0-2. Parasitemia (percentage of total erythrocytes infected with parasites) as a function of time was fit with an exponential growth equation. Whereas untreated parasite cultures grew normally in the presence of light, the growth of ALA-treated cultures was strongly attenuated by light (FIG. 4), consistent with a prior report (Smith, T. G. and Kain, K. C., *Journal of Infectious Diseases* 190, 184-191, 2004). Microscopic examination by blood smear revealed that ALA-treated cultures predominantly contained pyknotic parasites, indicative of widespread cell death. The photosensitivity of parasite growth in ALA was fully rescued by 50 µM succinylacetone, an ALA dehydratase (ALAD) inhibitor shown in previous work to substantially reduce PPIX biosynthesis from ALA in parasite-infected erythrocytes (Ke, H. et al. *J. Biol. Chem.* 289, 34827-34837, 2014; Nagaraj, V. A., et al. *PLoS Patholg.* 9, e1003522, 2013). This chemical rescue confirmed that parasite photosensitivity in ALA requires biosynthetic conversion of ALA to PPIX.

Figure 5A:
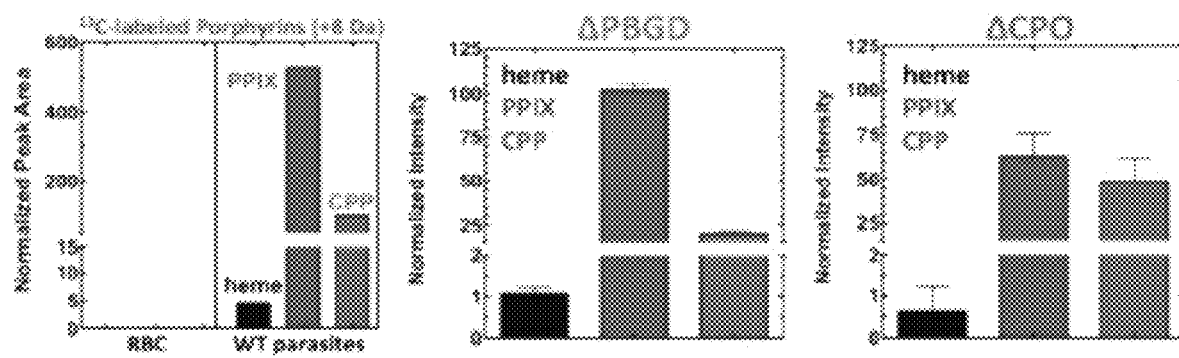
FIG. 5A, FIG. 5B, FIG. 5C, FIG. 5D and FIG. 5E illustrate that stable disruption of parasite enzymes and the apicoplast do not affect heme biosynthesis from ALA.
Figure 5B:
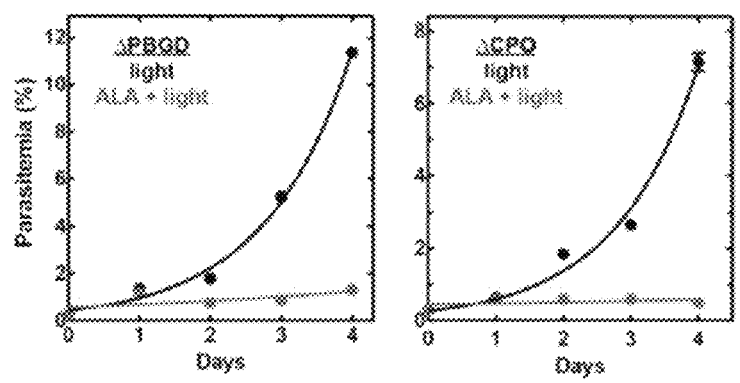

Example 2. Stable Disruption of Parasite Enzymes and the Apicoplast do not Affect Heme Biosynthesis from ALA Upstream enzymes in the parasite-encoded heme biosynthesis pathway are amenable to genetic disruptions that block production of PPIX from exogenous ALA (FIG. 1A) and thus prevent parasite photosensitivity. The parasite genes encoding the apicoplast-targeted porphobilinogen deaminase (PBGD) and cytosolic coproporphyrinogen III oxidase (CPO) were successfully disrupted using single-crossover homologous recombination to truncate the open reading frame for each gene. Southern blot and PCR analysis confirmed correct integration and gene disruption in clonal parasite lines. These genetic disruptions had no effect on the ability of parasite-infected erythrocytes to incorporate $^{13}$C-labelled ALA into heme, PPIX, or coproporphyrinogen III (FIG. 5A), as monitored by a previously developed tandem mass spectrometry assay (Ke, H. et al., *J. Biol. Chem.* 289, 34827-34837, 2014), and clonal growth of both parasite lines remained fully photosensitive in ALA (FIG. 5B). FIG. 5B depicts growth of asynchronous ΔPBGD (left) and ΔCPO (right) 3D7 parasites in the presence or absence of 200 µM ALA, with 2-minute light exposures on an overhead projector on days 0-2. WT growth was fit to an exponential equation.

Figure 5C:
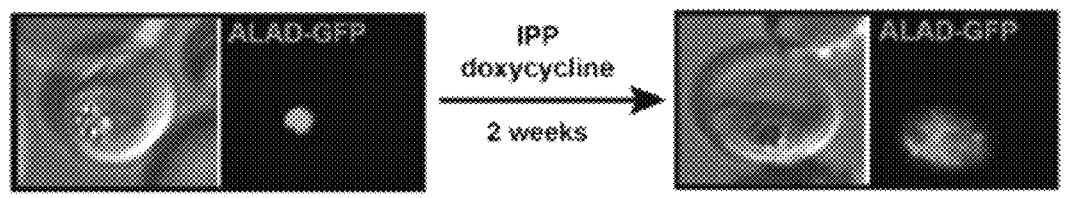
Figure 5D:
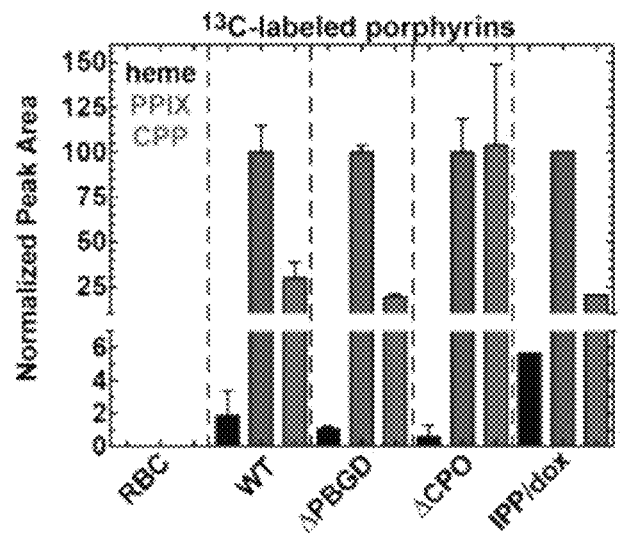
Figure 5E:
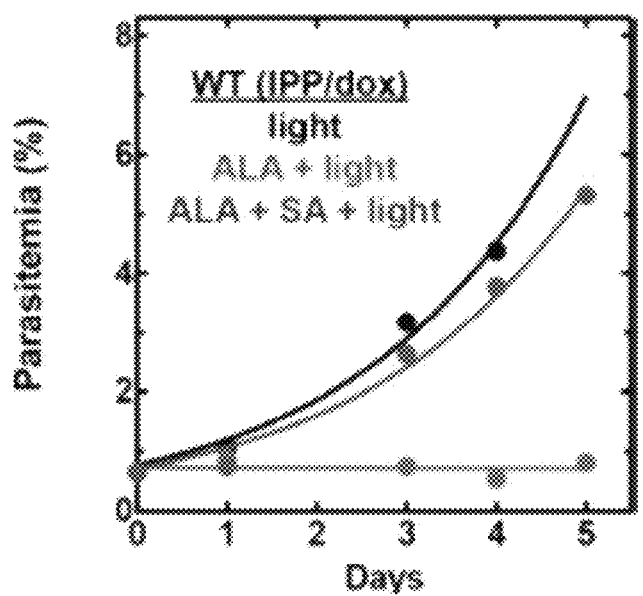

The present inventors stably disrupted this organelle by treating parasites with doxycycline and isopentenyl pyrophosphate (IPP). Doxycycline inhibits the prokaryotic replication machinery of the apicoplast and prevents organelle segregation, resulting in apicoplast loss and parasite death (Dahl, E. L., et al., *Antimicrob. Agents Chemother.* 50, 31243131, 2006). The lethal effects of doxycycline, however, can be chemically rescued by IPP, which enables parasites to make essential isoprenoids despite apicoplast disruption and leads to a stable metabolic state in which parasites lack the intact organelle such that nuclear-encoded proteins ordinarily targeted to the apicoplast become stranded in small vesicles. (Yeh, E. and DeRisi, J. L., *PLoS Biol.* 9, e1001138, 2011). Apicoplast loss in doxycycline and IPP-treated parasites was confirmed with microscopy to verify disrupted targeting of the nuclear-encoded ALAD enzyme (FIG. 5C). FIG. 5C depicts bright field and fluorescence images of live 3D7 parasites expressing ALAD-GFP from a plasmid before or after two-week treatment with IPP and doxycycline. Despite apicoplast disruption, these parasites retained their capacity for heme biosynthesis (FIG. 5D) and remained fully photosensitive in ALA (FIG. 5E). FIG. 5D illustrates LC-MS/MS detection of $^{13}$C-labelled heme, PPIX, and CPP in parasites grown in 200 µM 5-[$^{13}$C4]-ALA. Parasites were extracted in DMSO, supplemented with deuteroporphyrin as an internal standard, and analyzed by LC-MS/MS. Integrated analyte peak areas were normalized to PPIX in each sample. RBC: uninfected red blood cells, WT: parental clone 3D7, IPP/dox: isopentenyl pyrophosphate/doxycycline-treated 3D7 parasites. FIG. 5E illustrates growth of asynchronous IPP/doxycycline-treated parasites in the presence or absence of 200 µM ALA and 50 µM succinylacetone (SA), with 2-minute light exposures on an overhead projector on days 02. These results illustrate that parasite infected erythrocytes have a parallel biosynthetic pathway that bypasses functional disruption of the parasite enzymes targeted to the apicoplast and cytoplasm.

Figure 6:
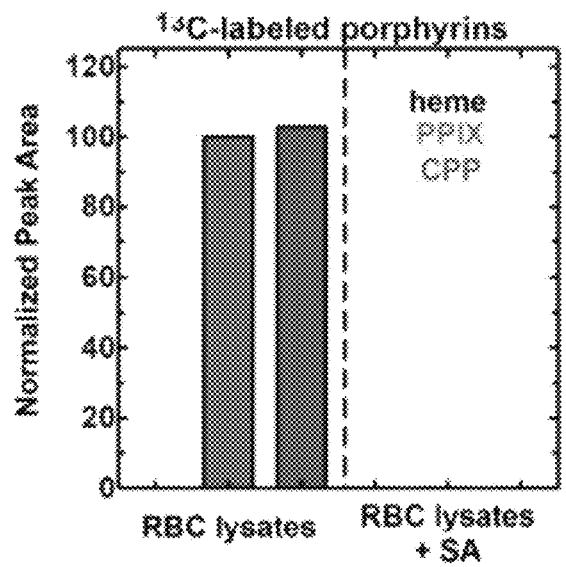
FIG. 6 illustrates that biosynthesis of PPIX and coproporphyrin III can be blocked by succinylacetone.

Example 3. Erythrocytes Retain Vestigial Heme Biosynthesis Enzymes with Latent Activity in ALA In these investigations, red porphyrin fluorescence in ALA-treated intraerythrocytic parasites was not limited to the parasitophorous vacuole but was detectable throughout the erythrocyte cytoplasm (FIG. 3A), as expected for host enzyme activity in this compartment and production of PPIX. To directly test the model that enzymes remaining in the erythrocyte cytoplasm could catalyze PPIX biosynthesis from ALA, the present inventors permeabilized uninfected erythrocytes using the plant-derived detergent saponin, clarified lysates by centrifugation (25,000×g for 60 min.) followed by sterile filtration (0.2 µM), and then used tandem mass spectrometry to monitor heme and porphyrin biosynthesis from $^{13}$C-labelled ALA added to the filtered lysate supernatant. The inventors detected formation of $^{13}$C-labelled PPIX and coproporphyrin III (the spontaneous oxidation product of the pathway intermediate coproporphyrinogen III) but not heme, and this biosynthetic activity was fully blocked by succinylacetone (FIG. 6). FIG. 6 depicts LC-MS/MS detection of $^{13}$C-labelled PPIX and CPP in erythrocyte lysate supernatants incubated with 200 µM 5-[$^{13}$C4]-ALA without or with 50 µM succinylacetone (SA). Erythrocytes were lysed in 0.04% saponin, centrifuged at 25,000×g for 60 min., and 0.2 µM syringe filtered prior to ALA addition. These data illustrate that erythrocytes retain a vestigial and partial biosynthesis pathway capable of converting exogenous ALA into PPIX but unable to convert PPIX to heme due to lack of mitochondria and ferrochelatase.

Figure 7A:
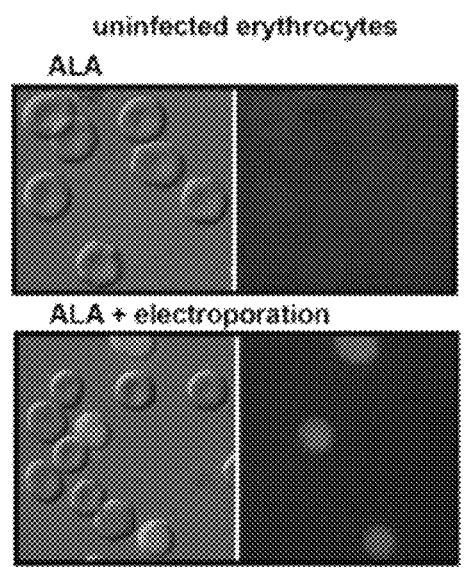
FIG. 7A, FIG. 7B, FIG. 7C and FIG. 7D illustrate that ALA uptake by erythrocytes requires permeability pathways established by *Plasmodium infection*.

Example 4. ALA Uptake by Erythrocytes Requires New Permeability Pathways Established by *Plasmodium* Infection In contrast to parasite-infected erythrocytes, uninfected erythrocytes showed no detectable porphyrin fluorescence in the presence of ALA (FIG. 7A), consistent with reports that the erythrocyte membrane has a general low permeability to small molecule zwitterions (Desai, S. A., et al., *Nature* 406, 1001-1005, 2000; Kirk, K., et al., *J. Biol. Chem.* 269, 3339-3347, 1994; Ginsburg, H., et al., *Mol. Biochem. Parasitol.* 14, 313-322, 1985). FIG. 7A depicts Bright field and fluorescence (Zeiss filter set 43 HE) images of uninfected erythrocytes incubated in 500 µM ALA before or after electroporation. Electroporation of uninfected erythrocytes in the presence of ALA resulted in robust intracellular porphyrin fluorescence (FIG. 7A), illustrating that host enzymes have latent biosynthetic activity that requires a mechanism for ALA uptake across the normally impermeable erythrocyte membrane.

Upon invasion, *Plasmodium* parasites export hundreds of effector proteins into host erythrocytes. These proteins dramatically alter the architecture of the infected erythrocyte and establish new permeability pathways (NPP) that enhance host cell uptake of amino acids and other nutrients from host serum (Spillman, N. J., et al., *Ann. Rev. Biochem.*, 84, 813-841, 2015 expected publication June 2015).

Figure 7B:
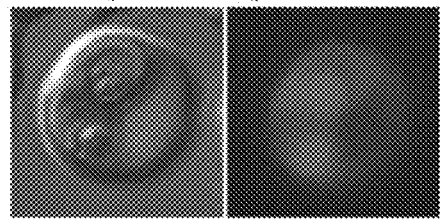
Figure 7B:
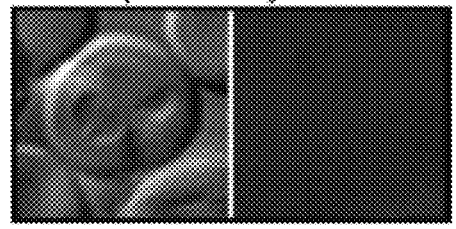
Figure 7C:
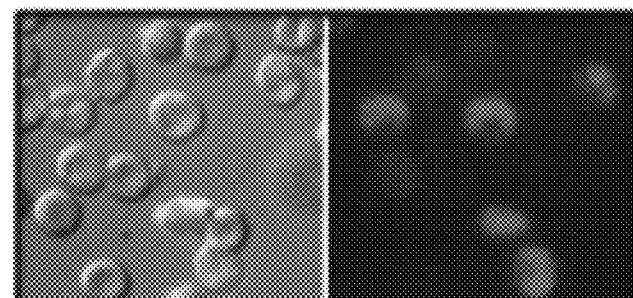
Figure 7C:
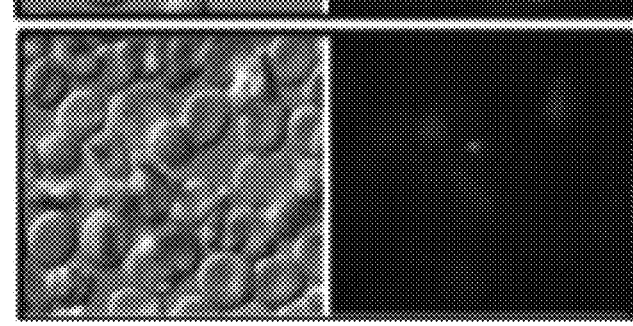
Figure 7D:
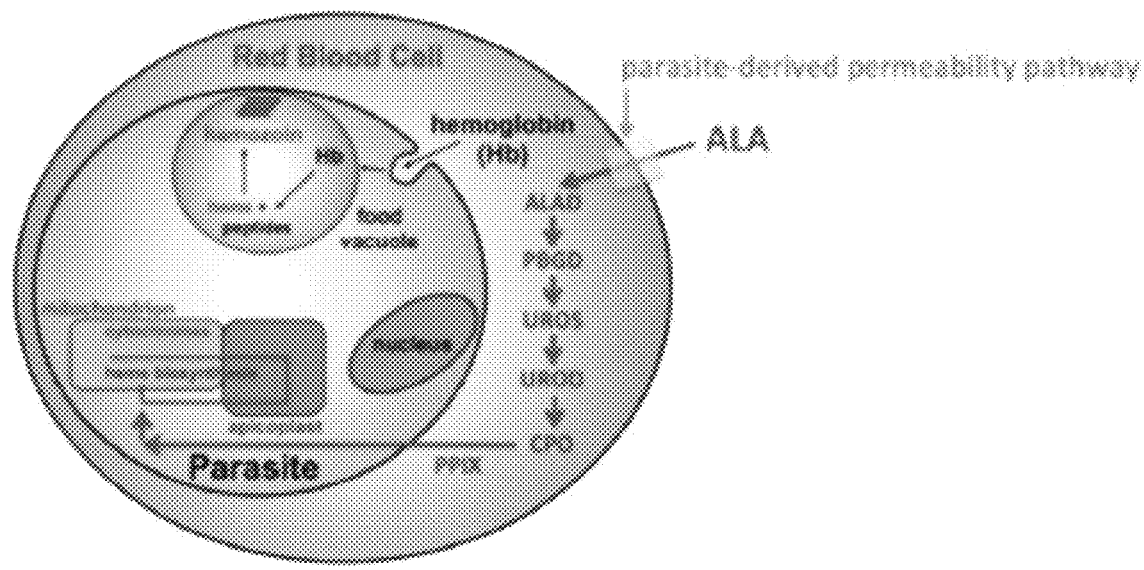

In an investigation of selective uptake of ALA by infected erythrocytes via parasite-dependent nutrient acquisition pathways, the inventors utilized a parasite line in which the export of parasite proteins into host erythrocytes, including establishment of nutrient permeability pathways, can be conditionally regulated with the small-molecule ligand trimethoprim (TMP; Beck, J. R., et al., *Nature* 511, 592-595, 2014). In these parasites, protein export and NPP mechanisms are retained in the presence of TMP but blocked in its absence. TMP was retained or washed out of a synchronized culture of late schizonts to retain or block protein export, respectively, parasites were allowed to rupture and reinvade new erythrocytes, and then both sets of parasites (i.e., ±TMP and thus ±NPP) were incubated in ALA for 8 hours. Whereas TMP-treated parasites with normal protein export and permeability displayed robust PPIX fluorescence indistinguishable from wild-type parasites, parasites whose protein export and establishment of NPP mechanisms were blocked by removing TMP showed no detectable PPIX fluorescence (FIG. 7B). FIG. 7B depicts Bright field and fluorescence images of parasites cultured in 500 µM ALA with normal (+TMP) or blocked (−TMP) establishment of parasite permeability pathways in the erythrocyte membrane. Infected erythrocyte permeability was modulated using a 3D7 parasite line expressing Hsp101 tagged at its endogenous locus with a trimethoprim (TMP)-dependent destabilization domain. TMP was maintained or washed out from synchronous schizont-stage parasites, which were allowed to rupture and invade new erythrocytes. 500 µM ALA was added to both cultures after invasion, and parasites were imaged 8 hours later. Similar results were achieved in wild-type parasites using the small-molecule drug furosemide, which blocks parasite-derived NPP mechanisms directly (FIG. 7C; Staines H M 2004 *Mol. Biochem. Parasitol.* 133, 315-318). These observations illustrate, without being limited by theory, that ALA can be selectively taken up by infected erythrocytes via parasite-dependent nutrient acquisition pathways and metabolized to PPIX within the erythrocyte cytoplasm (FIG. 7D). The present data further illustrate, without being limited by theory, that PPIX produced by host enzyme activity can then be taken up by parasites and converted to heme by *Plasmodium ferrochelatase* within the parasite mitochondrion (FIG. 7D).

Figure 8A:
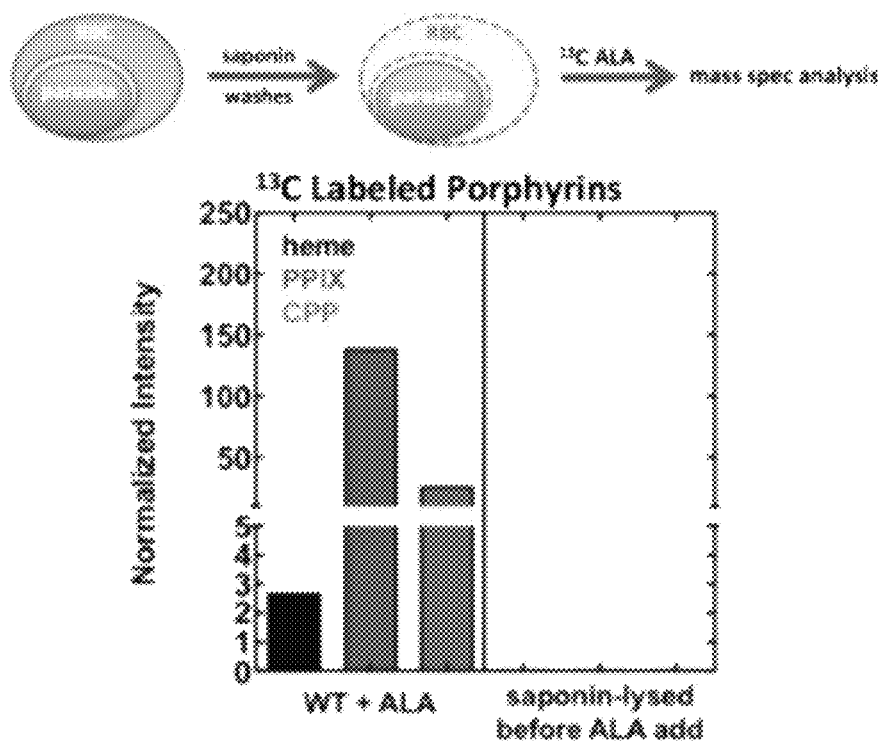
FIG. 8A, FIG. 8B and FIG. 8C illustrate that plasmodium-encoded heme biosynthesis pathway can have no detectable activity during blood-stage infection.

Example 5. *Plasmodium*-Encoded Heme Biosynthesis Pathway has no Detectable Activity During Blood-Stage Infection In these experiments, parasite-infected erythrocytes were biochemically fractionated using saponin to selectively permeabilize host cell membranes while leaving parasite membranes intact. Under these conditions, soluble erythrocyte proteins can be washed away to leave the intact parasite natively embedded within the resulting erythrocyte ghost. Parasites treated in this fashion remain metabolically active for 5-6 hours or longer, retain a transmembrane potential, accumulate fluorescent dyes such as MitaTracker® Red (Life Technologies), and carry out DNA synthesis (Cobbold, S. A., et al., *Int. J. Parasitol.* 41, 125-135, 2011; Izumo, A. et al., *Trans. R. Soc. Trop. Med. Hyg.* 81, 264-267, 1987). After saponin treatment and washout, parasites were placed back into culture medium containing $^{13}$C-ALA and incubated overnight before extraction for analysis by tandem mass spectrometry. Biosynthesis of heme, PPIX, or CPP in fractionated parasites was not detected (FIG. 8A), illustrating that the apicoplast-localized portion of the parasite heme biosynthesis pathway is largely or completely inactive during blood-stage infection.

Figure 8B:
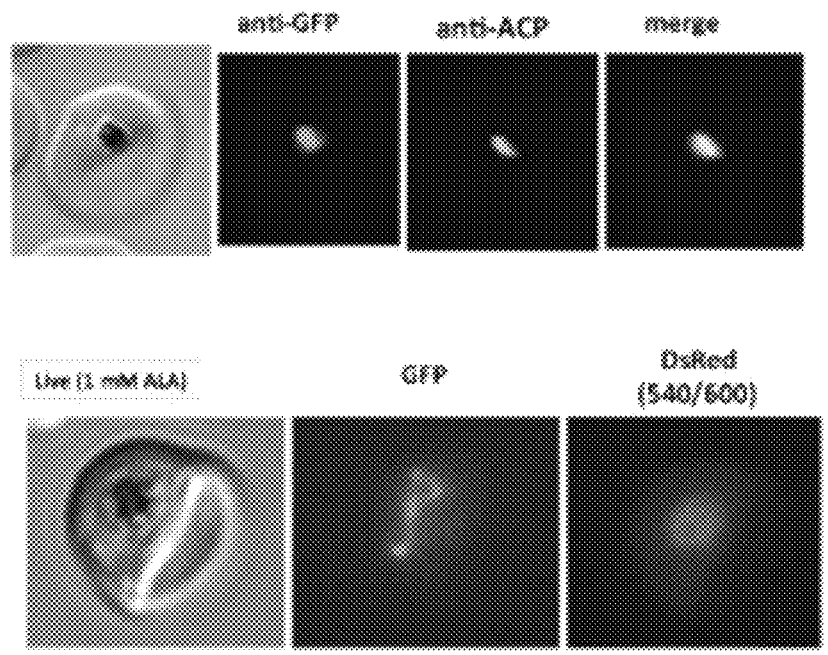
Figure 8C:
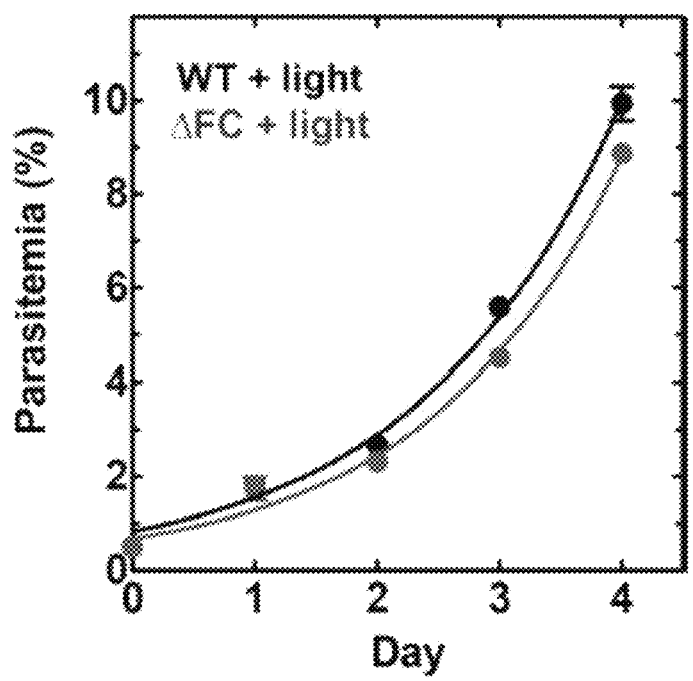

To test this conclusion within undisrupted parasites, the present inventors created a transgenic parasite line expressing an apicoplast-targeted copy of the uroporphyrinogen III methyltransferase (cobA) gene from *Propionibacterium freudenreichii* to serve as a biosensor of heme biosynthesis pathway activity within the parasite apicoplast. The cobA protein catalyzes a key step in bacterial cobalamin biosynthesis, converting the uroporphyrinogen III intermediate produced by the heme biosynthesis pathway into the red fluorescent product trimethylpyrrocorphin, and has been shown to function when heterologously expressed in bacteria, yeast, and mammalian cells (Sattler, I., et al., 1995 *J. Bacteria.* 177, 1564-1569; Wildt, S. and Deuschele, U., *Nat. Biotechnol.* 17, 1175-1178, 1999). These data confirm correct targeting of a cobA-GFP fusion protein to the apicoplast in ALA-treated parasites but were unable to detect any red fluorescence in the apicoplast indicative of cobA-mediated conversion of uroporphyrinogen III to trimethylpyrrocorphin (FIG. 8B), suggesting that parasite enzymes targeted to this organelle are inactive in both asexual and sexual blood stages. Growth of ΔFC parasites (Ke, H., et al., 2014, *J. Biol. Chem.* 289, 34827-34837), which would be expected to accumulate PPIX during native pathway activity (FIG. 1A), was insensitive to light in the absence of ALA (FIG. 8C). WT or ΔFC D10 parasites were cultured under normal growth conditions (without exogenous ALA) with two-minute light exposures on an overhead projector lightbox on days 0-2. Culture parasitemia as a function of time was fit to an exponential growth model. Both WT and ΔFC parasites had parasitemia doubling times of 1.1 days under these conditions (FIG. 8C). These observations illustrate that heme biosynthesis in blood-stage *P. falciparum* parasites is only operative when exogenous ALA is present to stimulate PPIX production by remnant host enzymes in the erythrocyte cytoplasm with subsequent PPIX uptake and conversion to heme by ferrochelatase in the parasite mitochondrion (FIG. 7D).

Figure 9A:
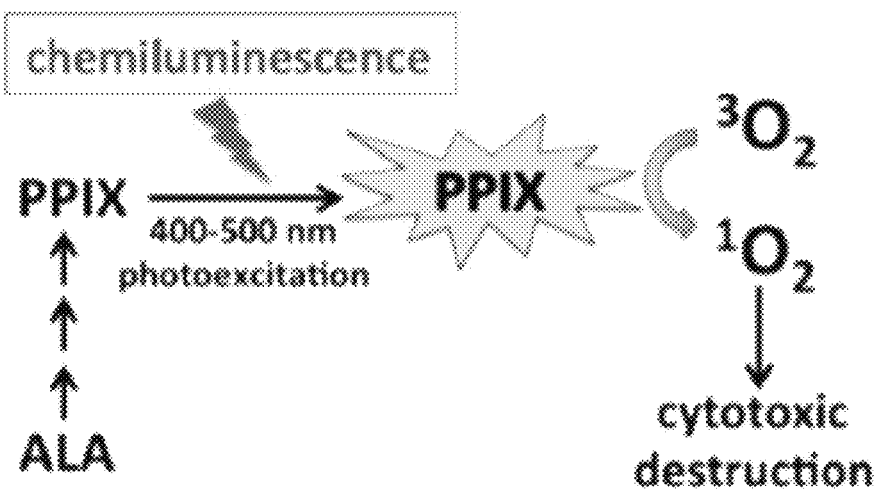
FIG. 9A and FIG. 9B illustrate chemiluminescence-based photodynamic therapy for treatment of bloodstage malaria.
Figure 9B:
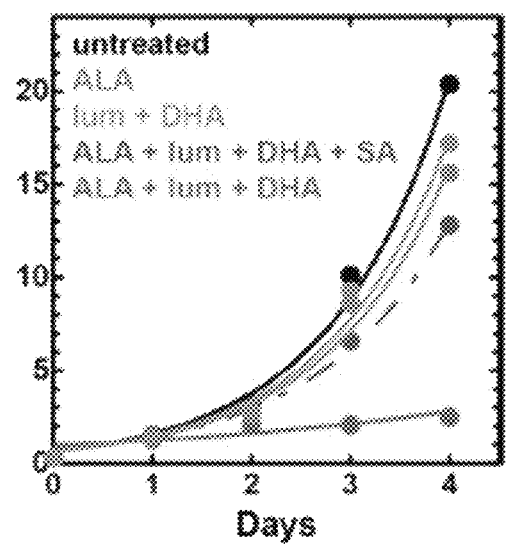

Example 6. Development of Chemiluminescence-Based Photodynamic Therapy for Treatment of Bloodstage Malaria The present inventors tested whether intraerythrocytic parasites might be uniquely susceptible to chemiluminescence-based photodynamic therapy (CL-PDT) (FIG. 9A). Artemisinin and its derivatives are current frontline drugs used for treatment of malaria, usually in combination with a partner drug. To test the efficacy of an artemisinin CL-PDT strategy for treatment of blood-stage malaria, we incubated intraerythrocytic parasites in 50-100 µM ALA with or without luminol and sub-therapeutic doses (≤10% of EC50) of dihyroartemisinin (DHA), with twice-daily media changes. Parasites treated with each compound in isolation or in combination with only one other compound showed little difference in growth rate compared to mock-treated parasites. The combination of all three compounds, however, resulted in potent inhibition of parasite growth (FIG. 9B), and microscopic examination by blood-smear revealed widespread evidence of pyknosis and parasite death. The cytotoxicity of this combination could be rescued by treatment with succinylacetone, supporting a photodynamic mechanism requiring heme biosynthetic flux.

The development of parasite resistance to frontline antimalarial drugs continues to hamper malaria treatment and eradication efforts worldwide. To test whether a CL-PDT mechanism remains effective against parasites with diverse resistance to distinct drugs, the inventors designed studies with Dd2 parasites, which have multidrug resistance to antifolate and quinolone antibiotics (Sidhu, A. B. S., et al., *Science* 298, 210-213, 2002), and with clinical isolates containing kelch-13 protein mutations that confer artemisinin tolerance (Ariey, F., et al., *Nature* 505, 50-55, 2014). In both parasite lines, combination treatment with ALA, luminol, and DHA potently ablated parasite growth. These data demonstrate that a CL-PDT combination with artemisinin provides a potent strategy for treatment of blood-stage malaria. All three compounds have excellent toxicity profiles and have each been used clinically (Larkin, T. and Gannicliffe, C., *Sci. Justice* 48, 71-75, 2008; Bissonnette, R., et al., *Photochem. Photobiol.* 74, 339-345, 2001; Gordi, T. and Lepist, E. I., *Toxicol. Lett.* 147, 99-107, 2004). Also, a CL-PDT strategy has the advantage of relying on the activity of host enzymes in the erythrocyte that are outside the genetic control of the parasite and thus refractory to development of resistance-conferring mutation.

All publications cited herein are incorporated by reference, each in their entirety.

What is claimed is:

1. A method of killing intraerythrocytic parasites, the method comprising contacting the parasites with therapeutically effective amount of a combination of 5-aminolevulinic acid or a derivative thereof, luminol or a derivative thereof, and artemisinin or a derivative thereof.

2. The method of claim 1, further comprising administering a therapeutically effective amount of 4-iodophenol.

3. The method of claim 1, wherein the artemisinin or derivative thereof is selected from the group consisting of artemisinin, artesunate, artemether, dihydroartesmisinin, artelinic acid, and artemotil.

4. The method of claim 1, wherein the artemisinin or derivative thereof is dihydroartesmisinin.

5. The method of claim 1, wherein the artemisinin or derivative thereof is administered at a sub-therapeutic dose.

6. The method of claim 5, wherein the sub-therapeutic dose is ≤10% of the $EC_{50}$ of the artemisinin or derivative thereof.

7. The method of claim 1, wherein the luminol or derivative thereof is selected from the group consisting of lumino, luminol sodium salt, luminol hemihydrate, luminol hydrochloride, isoluminol, isoluminol monohydrate, and N-(4-aminobutyl)-N-ethyl-isoluminol (ASEI).

8. The method of claim 1, wherein the 5-aminolevulinic acid or derivative thereof is selected from the group consisting of 5-aminolevulinic acid (5-ALA), methylaminolevulinate, hexylaminolevulinate, 5-ALA esters, and 5-ALA amides.

9. The method of claim 1, wherein the killing of intraerythrocytic parasites is indicative by pyknosis.

10. The method of claim 1, wherein the parasites are drug-resistant.

11. The method of claim 1, wherein the parasites are artemisinin-resistant.

12. A method of treating blood-stage malaria, the method comprising administering to a subject in need thereof, therapeutically effective amount of a combination of 5-aminolevulinic acid or a derivative thereof, luminol or a derivative thereof, and artemisinin or a derivative thereof.

13. The method of claim 12, further comprising administering a therapeutically effective amount of 4-iodophenol.

14. The method of claim 12, wherein the artemisinin or derivative thereof is selected from the group consisting of artemisinin, artesunate, artemether, dihydroartesmisinin, artelinic acid, and artemotil.

15. The method of claim 12, wherein the artemisinin or derivative thereof is dihydroartesmisinin.

16. The method of claim 12, wherein the artemisinin or derivative thereof is administered at a sub-therapeutic dose.

17. The method of claim 16, wherein the sub-therapeutic dose is ≤10% of the $EC_{50}$ of the artemisinin or derivative thereof.

18. The method of claim 12, wherein the luminol or derivative thereof is selected from the group consisting of lumino, luminol sodium salt, luminol hemihydrate, luminol hydrochloride, isoluminol, isoluminol monohydrate, and isoluminol ABEI.

19. The method of claim 12, wherein the 5-aminolevulinic acid or derivative thereof is selected from the group consisting of 5-aminolevulinic acid (5-ALA), methylaminolevulinate, hexylaminolevulinate, 5-ALA esters, and 5-ALA amides.

20. The method of claim 12, wherein the parasites are artemisinin-resistant.

\* \* \* \* \*